(12) United States Patent
Boese et al.

(10) Patent No.: US 7,502,642 B2
(45) Date of Patent: Mar. 10, 2009

(54) METHOD AND DEVICE FOR VISUALLY SUPPORTING AN ELECTROPHYSIOLOGICAL CATHETER APPLICATION

(75) Inventors: Jan Boese, Eckental (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 532 days.

(21) Appl. No.: 11/114,609

(22) Filed: Apr. 26, 2005

(65) Prior Publication Data

US 2005/0251028 A1 Nov. 10, 2005

(30) Foreign Application Priority Data

Apr. 27, 2004 (DE) .................. 10 2004 020 587

(51) Int. Cl.
*A61B 5/05* (2006.01)
(52) U.S. Cl. ...................... 600/424; 600/407
(58) Field of Classification Search ............. 600/407, 600/424, 428, 437, 509, 510
See application file for complete search history.

(56) References Cited

U.S. PATENT DOCUMENTS

| 5,274,551 | A | * | 12/1993 | Corby, Jr. ............... 600/433 |
| 5,687,737 | A |   | 11/1997 | Branham et al. |
| 5,871,019 | A |   | 2/1999  | Belohlavek |
| 5,951,475 | A | * | 9/1999  | Gueziec et al. .......... 600/425 |
| 6,516,046 | B1 | * | 2/2003 | Frohlich et al. ............ 378/65 |
| 7,123,255 | B2 | * | 10/2006 | Trousett et al. ........... 345/419 |
| 2003/0018250 | A1 | | 1/2003 | Trousset et al. |
| 2003/0093067 | A1 | | 5/2003 | Panescu |
| 2003/0187358 | A1 | | 10/2003 | Okerlund et al. |
| 2003/0199748 | A1 | * | 10/2003 | Camus et al. ............ 600/407 |
| 2004/0017935 | A1 | | 1/2004 | Avinash et al. |
| 2004/0077942 | A1 | * | 4/2004 | Hall et al. ................ 600/428 |
| 2004/0097805 | A1 | * | 5/2004 | Verard et al. ............ 600/428 |
| 2004/0097806 | A1 | * | 5/2004 | Hunter et al. ............ 600/434 |
| 2004/0152970 | A1 | * | 8/2004 | Hunter et al. ............ 600/424 |
| 2004/0215071 | A1 | * | 10/2004 | Frank et al. ............. 600/407 |
| 2005/0197564 | A1 | * | 9/2005 | Dempsey ................. 600/411 |

FOREIGN PATENT DOCUMENTS

| DE | 196 04 977 A1 | 8/1997 |
| DE | 199 53 308 A1 | 6/2000 |
| DE | 103 11 319 A1 | 11/2003 |
| DE | 103 33 563 A1 | 2/2004 |
| DE | 103 40 544 A1 | 3/2005 |
| DE | 103 40 546 A1 | 3/2005 |
| EP | 1 182 619 A2 | 2/2002 |
| EP | 1 189 175 A1 | 3/2002 |
| WO | WO 01/80763 A2 | 11/2001 |
| WO | WO 02/062265 A2 | 8/2002 |

* cited by examiner

*Primary Examiner*—Eric F Winakur
*Assistant Examiner*—Lawrence N Laryea (57) ABSTRACT

The present invention relates to a method for visually supporting an electrophysiological catheter application in the heart, in which, during the execution of the catheter application, 2D fluoroscopy images (13) of the area of the heart being treated are recorded with an x-ray image recording system (5) and displayed together with 3D mapping data (14) of the area being treated, said 3D mapping data having been prepared simultaneously. A feature of this method is that the 2D fluoroscopy images (13) are registered with the 3D mapping data (14), and said 3D mapping data (14) is displayed, from the same perspective as the 2D fluoroscopy images (13), alongside said 2D fluoroscopy images (13) or image content derived from these (14), or is superimposed over them in the display.

28 Claims, 7 Drawing Sheets

METHOD AND DEVICE FOR VISUALLY SUPPORTING AN ELECTROPHYSIOLOGICAL CATHETER APPLICATION

CROSS REFERENCE TO RELATED APPLICATIONS

This application claims priority to the German application No. 10 2004 020 587.6, filed Apr. 27, 2004 which is incorporated by reference herein in its entirety.

FIELD OF INVENTION

The present invention relates to a method for visually supporting an electrophysiological catheter application in the heart, in which, during the execution of the catheter application, 2D fluoroscopy images of the area of the heart being treated are recorded with an x-ray image recording system and displayed together with electroanatomical 3D mapping data of the area being treated, said 3-D mapping data having been prepared simultaneously. The invention also relates to a device for implementing this method.

BACKGROUND OF INVENTION

The treatment of cardiac dysrhythmias has changed significantly since the introduction of the technique for catheter ablation by means of high-frequency current. In this technique an ablation catheter is introduced under x-ray monitoring into one of the ventricles, via veins or arteries, and obliterates the tissue causing the cardiac dysrhythmias by means of high-frequency current. For catheter ablation to be completed successfully, it is necessary for the cause of the cardiac dysrhythmia to be precisely localized in the ventricle. This localization is effected by means of an electrophysiological investigation, in which electrical potential is recorded with spatial resolution by means of a mapping catheter introduced into the ventricle. This electrophysiological investigation, known as electroanatomical mapping, thus produces 3D mapping data that can be displayed on a monitor. The mapping function and the ablation function are therefore often combined in a single catheter, so that the mapping catheter may also function simultaneously as an ablation catheter.

A known electroanatomical 3D mapping method, as may be implemented—for example—with the CARTO system by the company Biosense Webster Inc., USA, or the ENSITE 3000 system by the company Endocardial Solutions Inc., St. Paul, USA, is based on electromagnetic principles. Three different magnetic alternating fields with low intensity are set up under the examination table. By means of electromagnetic sensors integrated in the tip of the mapping catheter it is possible to measure the voltage changes within the magnetic field that are induced by catheter movements, and—with the help of mathematical algorithms—to calculate the position of the mapping catheter at any point in time. By point-by-point mapping of the endocardial contour of a ventricle using the mapping catheter, with simultaneous recording of electrical signals, an electroanatomical, three-dimensional map is produced in which the electrical signals are displayed with color-coding.

In addition to electroanatomical 3D mapping systems of this type, there are also intracardial localization systems such as—for example—the Localisa system by the company Medtronic, Minneapolis, USA, which use localization of the catheter and design of a 3D image of the examined ventricle. The data obtained using a localization system of this type is also referred to in the patent application as 3D mapping data, since it delivers a comparable 3D image of the examination area.

SUMMARY OF INVENTION

During the ablation procedure, the catheter is guided with the help of simultaneously recorded fluoroscopy images or real-time display of the 3D mapping data. The cardiological anatomy of the patient, including the cardiac vessels, cannot be mapped in detail in the 2D fluoroscopy images. Even the orientation to the displayed 3D mapping data does not guarantee that the ventricle surface generated from this data corresponds exactly to the anatomical conditions, since this would require the endocardial surface to be mapped very closely on a point-by-point basis. The additional anatomical image information of the 2D fluoroscopy images is still available during the mapping procedure, but can only be used to a limited extent—if at all—since the operation of the mapping system demands the electrophysiologist's undivided attention, so that he or she is not usually able to accurately capture the relationship between the displayed 3D mapping data and the simultaneously displayed 2D fluoroscopy image. The acquisition of 3D mapping data therefore often results in the generation of a surface of the endocard in the ventricle to be treated, which only approximately corresponds to the actual anatomy of the ventricle, because anatomically relevant surface points of the endocard are not sufficiently mapped.

Furthermore, for reasons of cost and practicality, in many cases only the ablation catheter with the position sensors is displayed relative to the mapped endocard surface on the EP mapping system monitor. It would be desirable, however, for all catheters used to be displayed, in particular the loop of the lasso catheter which—in a pulmonary vein isolation process—is fixed in the ostium of the pulmonary vein to be isolated, as an aid to the process.

The two older, subsequently published patent applications from N. Rahn et al. 103 40 546.1 and 103 40 544.5 disclose methods for improving the orientation of the electrophysiologist in the performance of the catheter ablation. In these methods, cardiological 3D image data of the examination area is generated by means of an imaging modality before the catheter application. This 3D image data is superimposed positionally and topographically over the 3D mapping data during the catheter application, providing the observer with additional anatomical image information. However, this requires a 3D imaging procedure to be available in the examination lab. Furthermore, even this method only allows the catheter carrying the corresponding position sensors to be displayed on the screen.

On the basis of these problems, an object of the invention is to provide a method and device for visually supporting an electrophysiological catheter application in the heart, which facilitates improved orientation during the guidance of the catheter in the catheter application, particularly during electroanatomical mapping and/or a catheter ablation.

The object is achieved by the claims. Advantageous embodiments of the method and device are described in the dependent claims or may be obtained from the following description and the exemplary embodiments.

In this method for visually supporting an electrophysiological catheter application in the heart, during the execution of the catheter application 2D fluoroscopy images of the area of the heart being treated, for example a ventricle, are recorded with an x-ray image recording system and displayed together with 3D mapping data of the area being treated, said 3D mapping data having been prepared simultaneously. A feature of this method is that the 2D fluoroscopy images are registered with the 3D mapping data, and said 3D mapping data is displayed, from the same perspective as the 2D fluoroscopy images, in addition to said 2D fluoroscopy images or image content derived from these, or is superimposed over them in the display. The same perspective here means the same mapping perspective, i.e. on the same scale and viewed from the same direction. The 3D mapping data may be obtained in this context by means of an electroanatomical 3D mapping system or an intracardial localization system. A monoplane or biplane C-arm system is preferably used for recording the 2D fluoroscopy images. This system is particularly suited to catheter applications of this type owing to the improved accessibility to the examination area.

By registering the recorded 2D fluoroscopy images with the 3D mapping data, and displaying them together, from the same perspective, the relationship between the two images can immediately be seen by the electrophysiologist. This is certainly true if 3D mapping data is displayed separately alongside the corresponding 2D fluoroscopy images on a separate display, but is even more so, however, if the two images are displayed superimposed, as this enables the observer to see immediately which areas are not yet sufficiently recorded with the mapping system. A further advantage of the present invention is that the 2D fluoroscopy images also show the relevant current positions of all catheters and components located in them.

In one embodiment of the invention, the same display perspective may be achieved for a predefined position of the x-ray image recording system or a predefined 2D fluoroscopy image, by rotating the display of the 3D mapping data so that it shows the same perspective. In an alternative embodiment, the display is selected by the operator by interactively rotating the 3D mapping data, and the image recording system is controlled so that a 2D fluoroscopy image is thus recorded from the same perspective. The 3D mapping data and the 2D fluoroscopy images are therefore preferably recorded in the same phase of the cardiac cycle, to avoid inaccuracies as a result of cardiac movement. This synchronization with regard to the cardiac cycle phase can be achieved by timing the image recording system and the mapping system by means of the same ECG trigger unit.

The device for implementing this method therefore comprises one or more interfaces for input of the 3D mapping data and the image data from the 2D fluoroscopy images, a registration module for registering the 2D fluoroscopy images with the 3D mapping data, and, connected to the registration module, a display module that simultaneously displays the output data of the 3D mapping data, side-by-side or superimposed, with the corresponding 2D fluoroscopy image, from the same perspective, so that it can be viewed on a display unit, in particular a monitor. The device may therefore be configured as a component of the mapping system or of the image recording system, or even as a standalone device.

BRIEF DESCRIPTION OF THE DRAWINGS

The present method and the device operating according to it are explained again below in greater detail, with reference to the exemplary embodiments in conjunction with the drawings, in which.

DETAILED DESCRIPTION OF INVENTION

Figure 1:
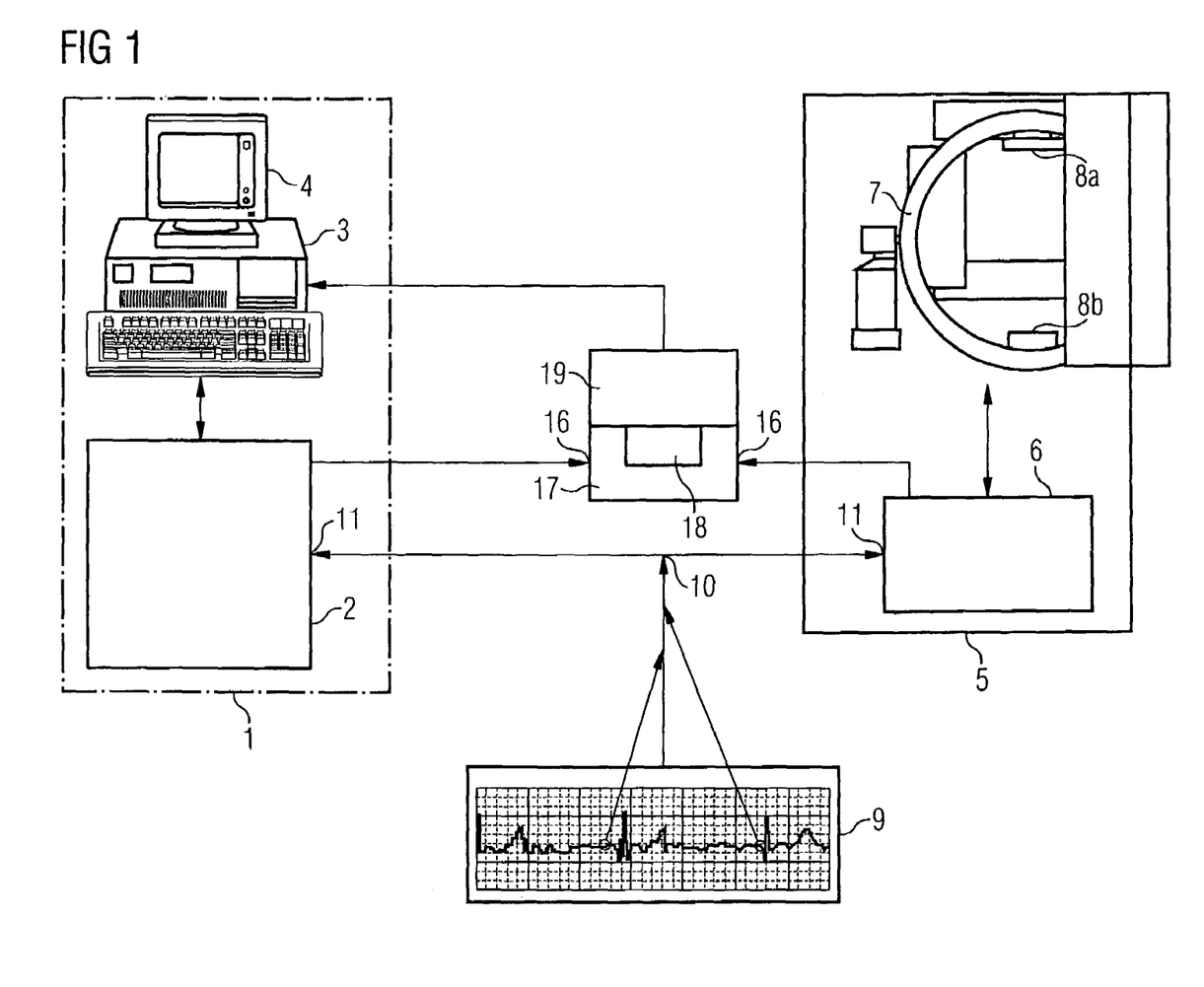
FIG. 1 shows an example of the simultaneous triggering of an x-ray image recording system and an EP mapping system for implementing this method.

FIG. 1 schematically illustrates a part of an EP mapping system 1 with a recording unit 2 for the 3D mapping data, which is connected to an analysis and image-processing unit 3 for displaying the captured data on a screen 4. Furthermore, by way of example, an x-ray system 5 in the form of a C-arm system is shown, said x-ray system having an image system 6 for providing the 2D fluoroscopy images. The C-arm system 5 comprises the C-arm 7, an x-ray source 8a, and x-ray detector 8b. In the known method, the C-arm 7 is designed such that it can be rotated about several axes. In this example an ECG is recorded from the patient, by means of an ECT recording system 9, during the catheter application. The ECG recording system 9 has a trigger output 10, which is connected to corresponding trigger inputs 11 on the image system 6 of the x-ray system 5 and to the recording unit 2 of the EP mapping system 1. This ECG triggering enables both the 3D mapping data and the 2D fluoroscopy images to be recorded, as shown in the displayed ECG in the lower part of the diagram, at a predefined phase in the cardiac cycle, as indicated by the circles at the foot of the diagram in the illustrated ECG. In this way, any interruption to the image recording or display caused by cardiac movement is avoided.

To implement this method, a 2D-3D registration of the 2D fluoroscopy images with 3D mapping data is required. This registration may be effected by known registration methods using the registration module 17 of the device, which is shown in schematic form in FIG. 1. In this example, the device comprises an interface 16 for inputting the 3D mapping data 14 and the image data from the 2D fluoroscopy images 13, the registration module 17 for registering the 2D fluoroscopy images 13 with the 3D mapping data 14, and, connected to the registration module, a display module 19 that simultaneously displays the output data of the 3D mapping data 14, side-by-side or superimposed, with the corresponding 2D fluoroscopy image 13, from the same perspective, so that it can be displayed on the monitor 4. A segmentation module 18, which can extract a contour of the ventricle wall from the x-ray images 13, is also shown in this example as a component of the registration module 17. This device may be configured as a component of the mapping system or of the image recording system, or even as a standalone device.

The result of each 2D-3D registration is a projection matrix, which enables each pixel of the 2D fluoroscopy image to be precisely allocated to a 3D point in the 3D mapping data. This projection matrix can therefore be used for displaying the 3D mapping data with the same position and orientation as the 2D fluoroscopy image, and for superimposing the two displays as required.

Figure 2:
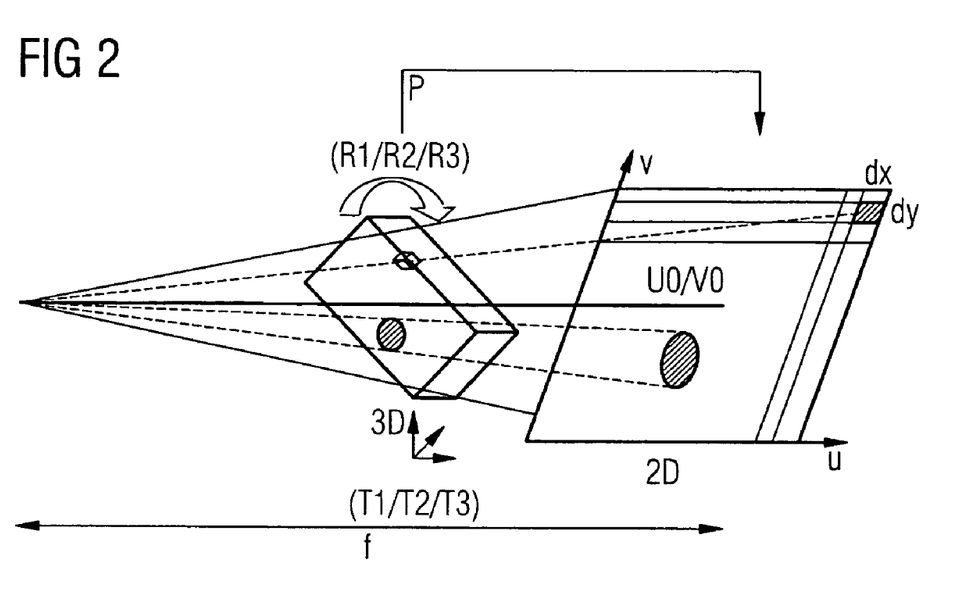
FIG. 2 illustrates the parameters necessary in the 2D/3D registration according to this method.

FIG. 2 illustrates the relationships in the 2D-3D registration. In this case, 11 degrees of freedom must be estimated for the projection matrix P. These 11 degrees of freedom correspond to 5 intrinsic parameters for each of the potential C-arm positions and 6 extrinsic parameters for the allocation of the coordination systems of the 3D mapping system and the x-ray image system. This projection matrix P is thus composed of a calibration matrix K for the image system, a rotation matrix R, and a translation matrix T:

$$P = K * R * T = \begin{pmatrix} f/dx & f*s & u_0 & 0 \\ 0 & f/dy & v_0 & 0 \\ 0 & 0 & 1 & 0 \\ 0 & 0 & 0 & 1 \end{pmatrix} * \begin{pmatrix} r11 & r12 & r13 & t1 \\ r21 & r22 & r23 & t2 \\ r31 & r32 & r33 & t3 \\ 0 & 0 & 0 & 1 \end{pmatrix}$$

The diagram illustrates the perspective mapping of a cuboid, representing the 3D mapping data, onto a two-dimensional image, representing the 2D fluoroscopy image. As a result of the projection, a spherical volume within the cuboid appears as a circle in the 2D image. The mapping can be calculated by the projection matrix P.

Figure 3:
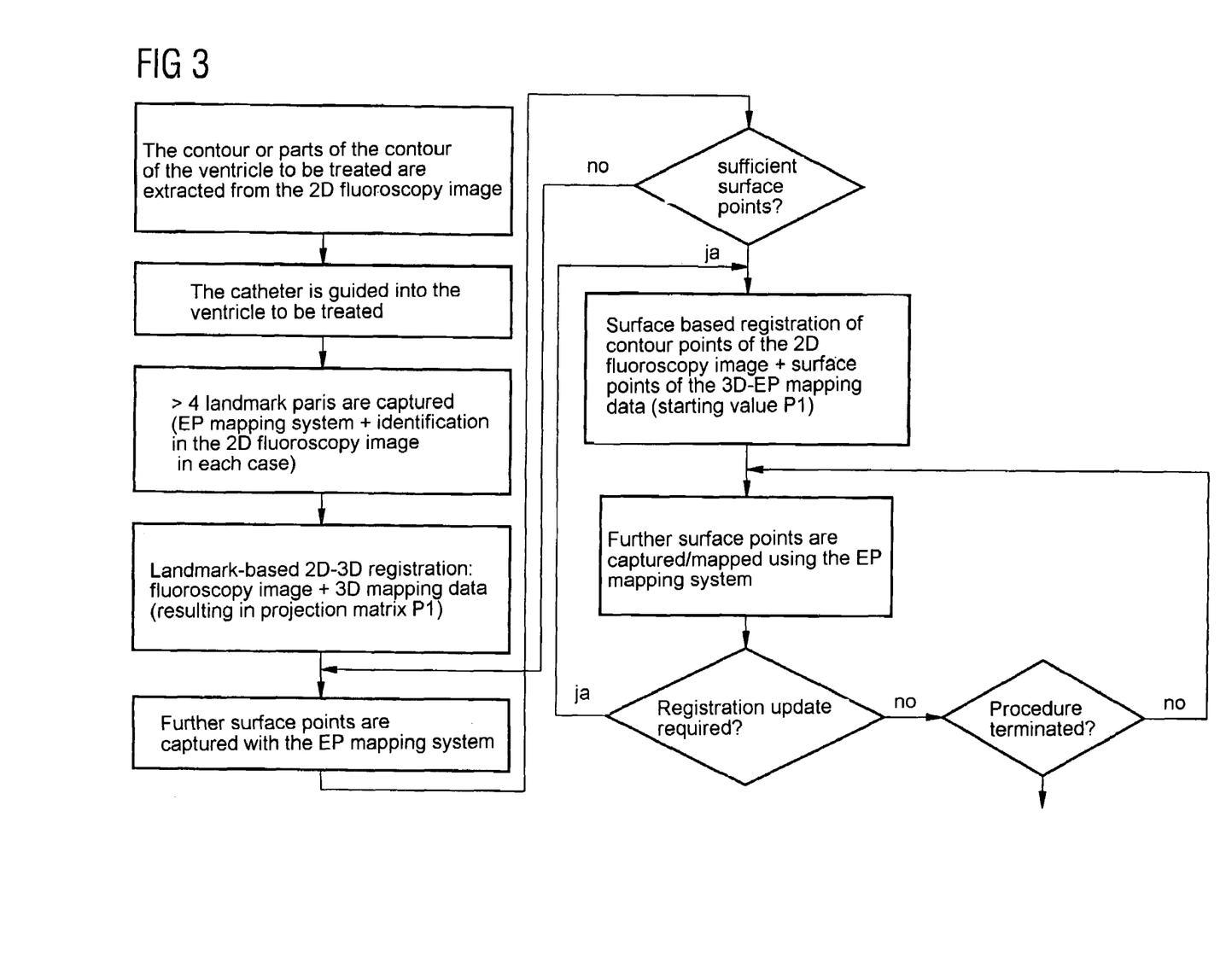
FIG. 3 shows an example of the registration process according to an exemplary embodiment of this method.

At the start of the mapping process, when only a very few surface points have been captured with the help of the EP mapping system, a landmark-based registration must be carried out since the surface of the 3D mapping data is as yet inadequately represented. Once a sufficient quantity of surface points of the mapping data is available, and the surface of the mapping data is adequately represented, the surface-based registration can be implemented. The result of the previous landmark-based registration can thus be used as a rough initial starting value for the surface-based registration. This procedure is illustrated in FIG. 3.

If the patient moves during the procedure, the projection matrix must be recalculated. This recalculation may be carried out by repeating the landmark-based or surface-based 2D-3D registration. Alternatively, the translation and rotation parameters required for recalculating the projection matrix may also be captured with the help of a position and orientation sensor attached to the patient.

Generally speaking, the projection matrix will also need to be recalculated if the C-arm is rotated or if the patient table is moved. This recalculation can likewise be carried out by repeating the landmark-based or surface-based 2D-3D registration. Alternatively, the translation and rotation parameters required for recalculating the projection matrix may be captured in this case with the help of position and orientation sensors attached to the patient table and C-arm.

Figure 4:
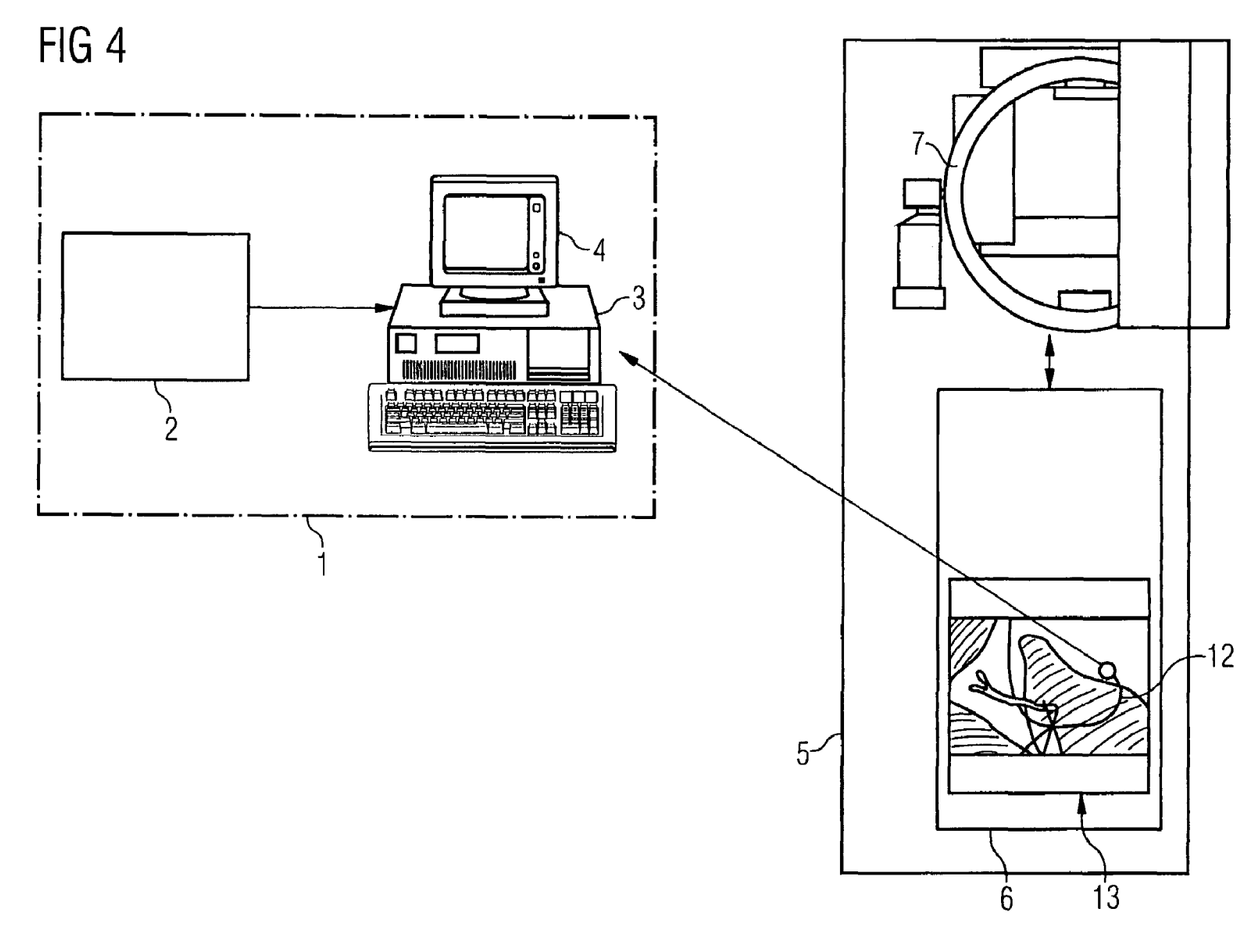
FIG. 4 illustrates the registration of landmark pairs by recording a surface point with the EP mapping system.

In the landmark-based 2D-3D registration, at least 4 landmarks are started, with the catheter, in the immediate vicinity of the ventricle to be treated or directly in the ventricle, and are thus identified in both the 2D fluoroscopy image and the 3D mapping data. If the position of the catheter can be automatically detected in the 2D fluoroscopy image with the help of a pattern detection algorithm, then the landmarks can be identified solely by operator interaction on the EP mapping system by recording an surface point. This may be seen in FIG. 4, which shows the position of the tip of the mapping catheter 12 in the 2D fluoroscopy image 13. If a landmark is started with this catheter, then the position of the catheter tip can be identified in the 2D fluoroscopy image 13 using the pattern detection process at the same time at which the position of this landmark is captured with the EP mapping system 1. This position is transferred to the EP mapping system 1, as indicated by the arrow. By recording the 3D position of a landmark using the EP mapping system, the 2D position is stored simultaneously in the 2D fluoroscopy image. Following the identification of 4 corresponding landmarks in both the 3D mapping data and the 2D fluoroscopy image, a projection matrix is automatically defined which can be used to allocate each pixel of the 2D fluoroscopy image precisely to a 3D point in the 3D mapping data. Of course, the catheter detection may also be carried out interactively by the operator in the 2D fluoroscopy image, if it cannot be done automatically.

Essentially, easily identifiable anatomical points are preferably used as landmarks for registration, such as—for example—the superior vena cava, the inferior vena cava, fossa, coronary sinus, the tricuspid valve in the right atrium or the 4 pulmonal veins and the mitral valve in the left atrium.

If the contour of the ventricle to be treated can be extracted from the 2D fluoroscopy image, then these contour points can be registered with the captured surface points of the 3D mapping data, in order thus to determine the parameters of the projection matrix. Since the contour of the ventricle cannot in practice be extracted from pure x-ray images, since the contrast is insufficient, an x-ray acquisition may be effected immediately after the injection of a contrast medium for the purpose of contour definition. The contrast medium injection enables part of the ventricle being treated, or the complete ventricle including vessels leading to or from it, to be mapped with higher contrast. It is therefore possible, for example, for only part of the left atrium, including a branched pulmonal vein, to be displayed with an x-ray acquisition following a contrast medium injection, or for the complete left atrium, including the 4 pulmonal veins, to be enhanced by means of a contrast medium and for the corresponding contours to be extracted from the 2D fluoroscopy image.

With the surface-based registration, and particularly in the point-to-point registration used in it, a structurally significant part of the ventricle to be treated is sufficient in order to carry out the registration. It is therefore necessary only to be able to extract any part of the contour from the 2D fluoroscopy image, and not the entire contour of the ventricular endocard, including vessels.

Another highly advantageous technique for registration, as may be used in this method, is the calculation of the intrinsic parameters of the projection matrix by offline calibration of all C-arm positions and orientations. These 5 intrinsic parameters of the projection matrix may be obtained by calibration on a one-off basis or repeatedly as required. The calibration may be effected using a suitable calibration phantom with x-ray marks. Once calibration is complete the intrinsic parameters are known for every potential C-arm position and orientation, so that a one-off landmark-based or surface-based 2D-3D registration is then sufficient in order to determine the 6 extrinsic parameters that then describe the relationship between the 3D coordinates system of the mapping system and the 3D coordinates system of the C-arm system. This preliminary calibration thus avoids the need to estimate all 11 degrees of freedom of the projection matrix again after each movement of the C-arm.

In one particularly advantageous embodiment of this method, both the intrinsic and the extrinsic parameters of the projection matrix are calculated in advance by offline calibration of all C-arm positions and orientations, and—in addition—by determination of a fixed relationship between the 3D coordinates system of the EP mapping systems and the 3D coordinates system of the C-arm system. Thus, for example, if the CARTO EP mapping system is used, the relationship between the two 3D coordinates systems is determined by capturing the geometrical arrangement of the under-bed transmission coils, and calculating a transformation between the 3D coordinates system of the CARTO system and the 3D coordinates system of the C-arm system from this. If a reference position and orientation sensor is also used during the EP procedure on the patient, as is normally the case in the aforementioned EP mapping system, the position and orientation information of the reference sensor can also be taken into account in the transformation.

The last-mentioned C-arm offline calibration and the determination of the fixed relationship between the 3D coordinates system of the EP mapping system and the 3D coordinates system of the C-arm system enable the 11 degrees of freedom of the projection matrix to be determined, without operator interaction, after acquisition of the relevant current C-arm position and orientation. In this case, accordingly, the 2D-3D registration may be effected during the EP procedure completely automatically, by a processing unit, without any action by the operator.

The aforementioned registration enables the 2D fluoroscopy image to be displayed together with the 3D mapping data on the monitor of the EP mapping system, with the same orientation, side-by-side or superimposed. The same orientation is obtained by applying the projection matrix to the 3D mapping data. The orientation of this 3D mapping data is thus altered such that it corresponds to the viewing direction from which the 2D fluoroscopy image was recorded. A superimposed image display obtained in this way can be seen on the left of FIG. 5 by way of example. The surface points 14 of the 3D mapping data are thus stored with the 2D fluoroscopy image 13, in which the left inferior pulmonal vein, including branches, can be seen following the contrast medium injection. This is indicated by the arrow. In this way the operator can decide immediately whether further surface points around the pulmonal vein visible in the x-ray image should be captured with the EP mapping system, in order to display the anatomy in this area accurately.

Figure 5:
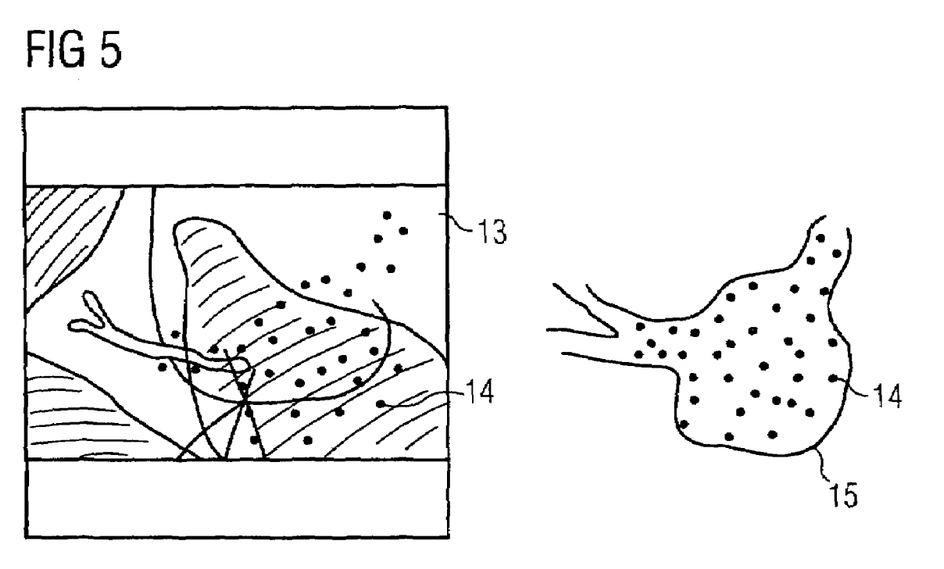
FIG. 5 shows two examples illustrating the superimposition of 3D mapping data and a 2D fluoroscopy image or image content derived therefrom.

If the contour of the ventricle to be treated can be extracted from the 2D fluoroscopy image, for example following injection of a contrast medium, it is therefore possible for just the contour of the 2D fluoroscopy image to be superimposed over the display of the 3D mapping data, as illustrated on the right of FIG. 5. Here, too, the 3D surface points 14 of the 3D mapping data can be identified. The extracted contour 13 of the left atrium, including two pulmonal veins, is superimposed on these. The stored contour of the left atrium enables the operator to decide whether further surface points should be captured with the EP mapping system in order to capture the anatomy in accordance with the actual contour.

If views of the 3D mapping data other than the view from the recording direction of the current 2D fluoroscopy image are to be displayed in combination, for each of these displays an additional 2D fluoroscopy image must be recorded with the corresponding perspective and a 2D-3D registration of the 2D fluoroscopy image with the 3D mapping data is necessary. In practice, it may be sufficient for 2 x-ray images to be used, with the viewing angle varying by 60°, for example, and for these two preferred directions to be registered once with the 3D mapping data. The C-arm may then be moved to and fro between these two preferred directions, possibly even automatically, without the need to repeat the registration. It is also possible, of course, to use a biplane C-arm system in which the 2D-3D registration is carried out for each of the two C-arm recording systems.

Of course, the images in question do not necessarily have to be displayed on the monitor of the EP mapping system, but may also be displayed on a standalone display unit or on the monitor of the x-ray system.

Figure 6:
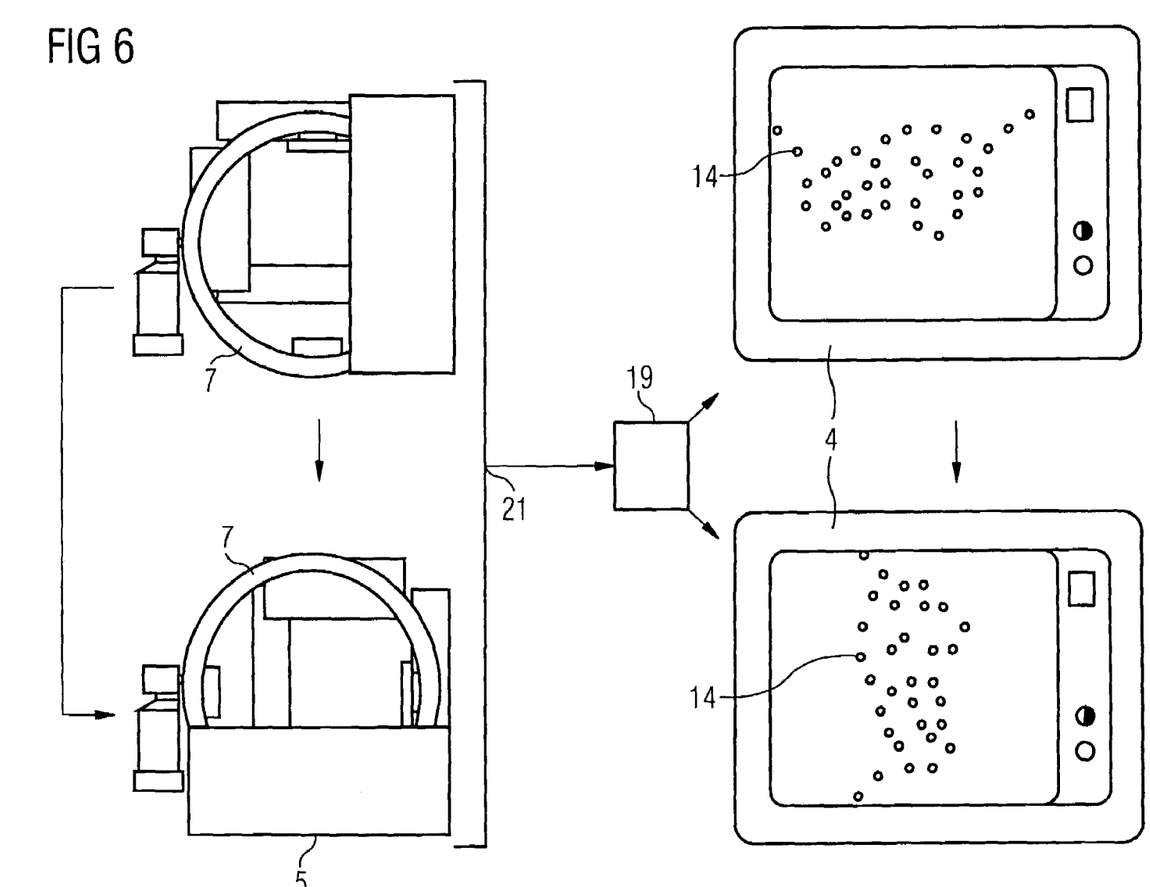
FIG. 6 shows an example of the variation in the display of 3D mapping data as a function of the position of the image recording system.

In a preferred embodiment of this method and associated device, following the 2D-3D registration for the current C-arm position the EP mapping system is switched to a mode in which the viewing orientation of the 3D mapping data is adjusted in real time to the current orientation of the C-arm 7. The image displayed thus rotates when the C-arm is moved. For this purpose the position parameters of the C-arm 7 are transferred, via a hardware interface 21—for example an Ethernet interface—from the x-ray system 5 via the display unit 19 to the EP mapping system 1, in which the viewing orientation of the 3D mapping data is then changed depending on the current position of the C-arm 7, in order to receive the same perspective. This synchronization principle is illustrated in FIG. 6, in which a change in the C-arm position is shown on the left. This change in position causes the viewing orientation of the 3D mapping data 14 displayed on the monitor 4 to change, as can be seen on the right of the diagram.

Figure 7:
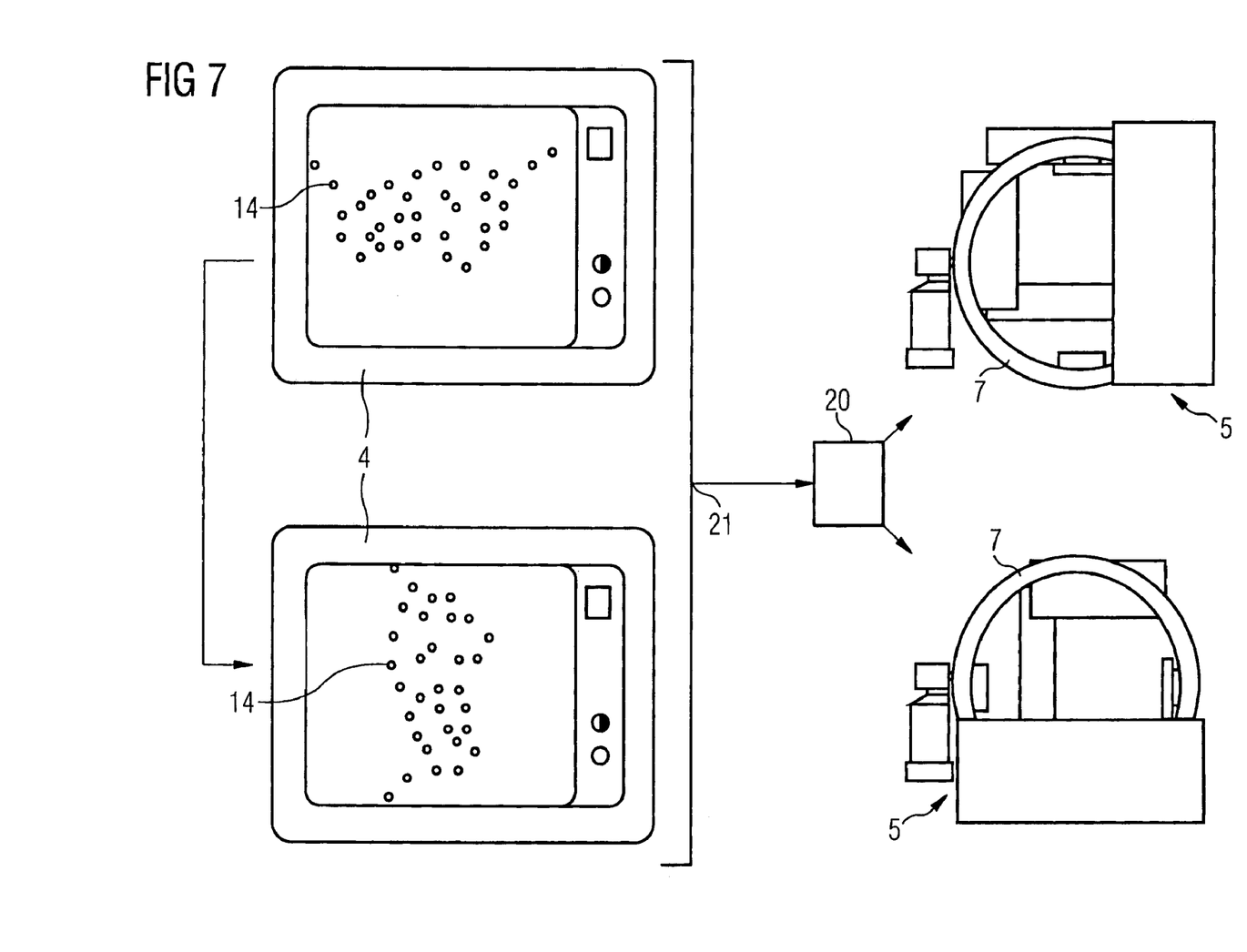
FIG. 7 shows an example of the control of the image recording system when the display of the 3D mapping data is changed interactively.

In a further embodiment of this method and corresponding device, the display of the 3D mapping data on the monitor 4 can be changed interactively by rotation. Following the 2D-3D registration for the current C-arm position, the EP mapping system 1 can be switched to a mode in which changing the viewing orientation of the 3D mapping data results in rotation of the C-arm 7. This is effected by means of a corresponding control module 20. The C-arm 7 is moved into a position in which the 2D fluoroscopy images, when recorded, correspond to the current viewing orientation of the 3D mapping data. The C-arm 7 thus moves according to the interactive rotation of the 3D mapping data on the display. For this purpose, parameters of the current orientation of the 3D mapping data are transferred, via a hardware interface 21, from the EP mapping system 1 to the control module 20, which then controls the x-ray system 5 such that the C-arm 7 is moved according to the orientation of the 3D mapping data. This synchronization principle is illustrated in FIG. 7. Interactively changing the orientation of the 3D mapping data 14 displayed on the monitor 4 causes the C-arm 7 to move to a new position and orientation, in which a recorded 2D fluoroscopy image would correspond to the same perspective as the changed display of the 3D mapping data. In this way the image can be displayed with the correct perspective whenever a 2D fluoroscopy image is recorded.

The invention claimed is:

1. A method of visually supporting heart examination or treatment using a catheter, the method comprising:
    inserting an electrophysiological catheter and catheters operative in conjunction therewith into the heart of a patient;
    recording 2D fluoroscopy images of an area of the heart under examination or treatment by an x-ray image recording system;
    determining 3D mapping data of the area generated by the electrophysiological catheter;
    determining a projection matrix relating the 3D mapping data and the 2D fluoroscopy image;
    applying the projection matrix to the 3D mapping data to orient the 3D mapping data to correspond to the viewing direction of the 2D fluoroscopy image; and to allocate pixel of the 2D fluoroscopy image to 3D points in the 3D mapping data;
    displaying the 3D mapping data side-by-side or simultaneously with the 2D fluoroscopy image, wherein the 3D mapping data and the 2D fluoroscopy images have the same display perspective, comprising a same display scale and viewed from a same orientation, and wherein the 2D fluoroscopy images show a current position of the electrophysiological catheter and the catheters operative in conjunction therewith.

2. The method according to claim 1, wherein the 3D mapping data are displayed next to the 2D fluoroscopy images.

3. The method according to claim 1, wherein the 3D mapping data are displayed next to an image content derived from the 2D fluoroscopy images.

4. The method according to claim 3, wherein the image content derived from the 2D fluoroscopy images is a contour of an object present in the area, the contour derived by segmenting the 2D fluoroscopy images.

5. The method according to claim 1, wherein the 2D fluoroscopy images are superimposed by the 3D mapping data.

6. The method according to claim 1, wherein the display perspective of the 3D mapping data is adjusted using an interactive rotation of the display of the 3D mapping data, and the x-ray image recording system is configured to record the 2D fluoroscopy images from a display perspective according to the adjusted display perspective of the 3D mapping data.

7. The method according to claim 1, wherein determining the 3D mapping data includes recording landmarks of the area, the landmarks identifiable in the 2D fluoroscopy images.

8. The method according to claim 1, further comprising registering the 2D fluoroscopy images with the 3D mapping data including adapting a surface, the adapting of the surface including matching a 3D surface shape of at least part of the area with at least one contour of at least part of the area, the 3D surface shape determined from the 3D mapping data, and the contour of at least part of the area determined from the 2D fluoroscopy images.

9. The method according to claim 1, wherein the x-ray image recording system is calibrated relative to a plurality of different display perspectives.

10. The method according to claim 9, further comprising determining a position of a 3D coordinate system assigned to the x-ray image recording system relative to a 3D coordinate system assigned to the 3D mapping data.

11. The method according to claim 10, wherein the x-ray image recording system is calibrated relative to two different display perspectives, and the 2D fluoroscopy images are recorded relative to the two different display perspectives.

12. The method according to claim 10, wherein registering the 2D fluoroscopy images with the 3D mapping data is carried out automatically based on the calibration and the determined position.

13. The method of claim 1 wherein the projection matrix has a calibration portion, a rotation portion and a translation portion, the projection matrix for use in displaying the 2D fluoroscopy images and the 3D mapping data with the same display perspective.

14. The method of claim 13 wherein the catheter is inserted into a patient and wherein when the patient table is moved the projection matrix is recalculated.

15. The method of claim 1 wherein the steps of recording 2D fluoroscopy images and determining 3D mapping data are initiated by a common trigger.

16. A device for visually supporting heart examination or treatment using a catheter, the device comprising:
at least one input interface for simultaneously acquiring 3D mapping data generated by a catheter and image data corresponding to 2D fluoroscopy images generated by an x-ray image recording system;
a registration module configured for registering the 2D fluoroscopy images with the 3D mapping data using a projection matrix that relates the 3D mapping data and the 2D fluoroscopy images by applying the projection matrix to the 3D mapping data to orient the 3D mapping data to correspond to the viewing direction of the 2D fluoroscopy image pad to allocate pixels of the 2D fluoroscopy images to 3D points in the 3D mapping data; and
a display module connected to the registration module, wherein the display module is configured to simultaneously display the 3D mapping data and the 2D fluoroscopy images relative to the same display perspective, comprising a same display scale and viewed from a same direction, and wherein the 2D fluoroscopy images show a current position of the catheter.

17. The device according to claim 16, wherein the 3D mapping data are displayed next to the 2D fluoroscopy images.

18. The device according to claim 16, wherein the 3D mapping data are displayed next to an image content derived from the 2D fluoroscopy images.

19. The device according to claim 18, further comprising a segmentation module for segmenting the 2D fluoroscopy images, the segmentation module configured to determine a contour of an area of the heart under examination or treatment, the contour being the image content derived from the 2D fluoroscopy images.

20. The device according to claim 16, wherein the 2D fluoroscopy images are superimposed by the 3D mapping data.

21. The device according to claim 16, wherein registering the 2D fluoroscopy images with the 3D mapping data includes processing landmarks included in the 3D mapping data, the landmarks identifiable in the 2D fluoroscopy images.

22. The device according to claim 16, wherein the registration module is configured to execute the registration by applying a surface matching algorithm.

23. The device according to claim 22, wherein the registration module is configured to execute the registration in a first rough and a second refined step, the first rough step comprising processing landmarks included in the 3D mapping data, the landmarks identifiable in the 2D fluoroscopy images, and the second refined step comprising the surface matching algorithm.

24. The device according to claim 23, wherein the surface matching algorithm comprises matching a 3D surface shape of at least part of the area with at least one contour of at least part of the area, the 3D surface shape determined from the 3D mapping data, and the contour of at least part of the area determined from the 2D fluoroscopy images.

25. The device according to claim 24, wherein the area is a heart ventricle.

26. The device according to claim 16, wherein the registration module is configured for automatically registering the 2D fluoroscopy images with the 3D mapping data based on calibrating data of an image recording system for recording the 2D fluoroscopy images and on a position of a 3D coordinates system assigned to the image recording system relative to a 3D coordinates assigned to the 3D mapping data.

27. The device according to claim 16, wherein the display module is configured for automatically adjusting a display perspective of the 3D mapping data based on a current recording setting of the image recording system.

28. The device according to claim 16, further comprising a control module for controlling an image recording system for recording the 2D fluoroscopy images, wherein controlling the image recording system includes interactively rotating the display of the 3D mapping data for adjusting a recording position of the image recording system to be in compliance with a display perspective of the 3D mapping data corresponding to the rotated display.

* * * * *